United States Patent [19]
Sawamura et al.

[11] Patent Number: 5,962,260
[45] Date of Patent: Oct. 5, 1999

[54] RECOMBINANT PRODUCTION OF HUMAN AND BOVINE RECEPTORS FOR MODIFIED LOW-DENSITY LIPOPROTEIN

[75] Inventors: Tatsuya Sawamura; Tomoo Masaki, both of Kyoto, Japan

[73] Assignee: Nippon Chemiphar Co., Ltd., Tokyo, Japan

[21] Appl. No.: 08/809,494

[22] PCT Filed: Nov. 30, 1995

[86] PCT No.: PCT/JP95/02444

§ 371 Date: Mar. 24, 1997

§ 102(e) Date: Mar. 24, 1997

[87] PCT Pub. No.: WO96/17058

PCT Pub. Date: Jun. 6, 1996

[30] Foreign Application Priority Data

Nov. 30, 1994 [JP] Japan ................................. 6-321705
Jul. 31, 1995 [JP] Japan ................................. 7-214206

[51] Int. Cl.$^6$ .................... C12N 15/12; C07K 14/705
[52] U.S. Cl. .................. 435/69.1; 536/23.5; 435/320.1; 435/7.1; 530/350
[58] Field of Search .................... 435/7.1, 69.1, 435/252.3, 320.1, 325, 21; 530/300, 350; 536/23.1, 23.5

[56] References Cited

U.S. PATENT DOCUMENTS

| 5,208,144 | 5/1993 | Smith et al. | 435/6 |
| 5,380,747 | 1/1995 | Medford et al. | 514/423 |
| 5,510,466 | 4/1996 | Krieger et al. | 530/395 |
| 5,665,872 | 9/1997 | Saito et al. | 536/23.5 |

OTHER PUBLICATIONS

Ngo et al. (1994) In: The Protein Folding Problem and Tertiary Structure Prediction Merz et al (eds) Birkhäuser, Boston, pp. 433, 492–495.

Ueda et al. (1993) Atherosclerosis 101:25–35 Abstract.

Itakura et al. (1990) LIPID 1:82–90–Abstract.

Mazzone et al (1982) Arteriosclerosis 2:487–497 Abstract.

*Primary Examiner*—David L. Fitzgerald
*Attorney, Agent, or Firm*—McAulay Nissen Goldberg Kiel & Hand, LLP

[57] ABSTRACT cDNAs encoding the human and bovine vascular endothelial receptors for modified low-density lipoprotein are provided. Also described are corresponding expression vectors, their use in the recombinant production of the encoded receptors, and the receptor polypeptides obtained thereby.

9 Claims, 3 Drawing Sheets

SEQUENCE LISTING

```
(1) GENERAL INFORMATION:

(iii) NUMBER OF SEQUENCES: 8

(2) INFORMATION FOR SEQ ID NO:1:

(i) SEQUENCE CHARACTERISTICS:
         (A) LENGTH: 1897 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Bos taurus
         (F) TISSUE TYPE: Vascular endothelial cells (vii) IMMEDIATE SOURCE:
         (A) LIBRARY: Bovine aortic endothelial cell cDNA
         (B) CLONE: pBLOX-1

(ix) FEATURE:
         (A) NAME/KEY: polyA_site
```

-continued

```
            (B) LOCATION: 1880..1897

(ix) FEATURE:
         (A) NAME/KEY: misc_RNA
         (B) LOCATION: 1859..1864
         (D) OTHER INFORMATION: /function= "PolyA Signal"

(ix) FEATURE:
         (A) NAME/KEY: 5'UTR
         (B) LOCATION: 1..34

(ix) FEATURE:
         (A) NAME/KEY: 3'UTR
         (B) LOCATION: 848..1897

(ix) FEATURE:
         (A) NAME/KEY: CDS
         (B) LOCATION: 35..847

(xi) SEQUENCE DESCRIPTION: SEQ ID NO:1:

GCTTCACTCT CTCATTCTTG GAATACATTT GAAA ATG ACT GTT GAT GAC CCC            52
                                     Met Thr Val Asp Asp Pro
                                       1               5

AAG GGT ATG AAA GAT CAA CTT GAT CAG AAG CCA AAT GGC AAG ACA GCA         100
Lys Gly Met Lys Asp Gln Leu Asp Gln Lys Pro Asn Gly Lys Thr Ala
         10                  15                  20

AAA GGT TTT GTT TCC TCT TGG AGG TGG TAC CCT GCT GCT GTG ACT CTA         148
Lys Gly Phe Val Ser Ser Trp Arg Trp Tyr Pro Ala Ala Val Thr Leu
 25                  30                  35

GGG GTC CTT TGT CTG GGA TTA CTG GTG ACT GTT ATA TTG TTA ATA CTG         196
Gly Val Leu Cys Leu Gly Leu Leu Val Thr Val Ile Leu Leu Ile Leu
 40                  45                  50

CAA TTA TCC CAG GTC TCT GAT CTC ATA AAG AAA CAG CAA GCA AAT ATT         244
Gln Leu Ser Gln Val Ser Asp Leu Ile Lys Lys Gln Gln Ala Asn Ile
 55                  60                  65                  70

ACT CAC CAG GAA GAT ATC CTG GAG GGA CAG ATT TTA GCC CAG CGC CGA         292
Thr His Gln Glu Asp Ile Leu Glu Gly Gln Ile Leu Ala Gln Arg Arg
             75                  80                  85

TCA GAA AAA TCT GCC CAG GAG TCA CAG AAG GAA CTC AAA GAA ATG ATA         340
Ser Glu Lys Ser Ala Gln Glu Ser Gln Lys Glu Leu Lys Glu Met Ile
             90                  95                 100

GAA ACC CTT GCC CAC AAG CTG GAT GAG AAA TCC AAG AAA CTA ATG GAA         388
Glu Thr Leu Ala His Lys Leu Asp Glu Lys Ser Lys Lys Leu Met Glu
            105                 110                 115

CTT CAC CGC CAG AAC CTG AAT CTC CAA GAA GTT CTG AAA GAG GCA GCA         436
Leu His Arg Gln Asn Leu Asn Leu Gln Glu Val Leu Lys Glu Ala Ala
        120                 125                 130

AAC TAT TCA GGT CCT TGT CCC CAA GAC TGG CTC TGG CAT GAA GAA AAC         484
Asn Tyr Ser Gly Pro Cys Pro Gln Asp Trp Leu Trp His Glu Glu Asn
135                 140                 145                 150

TGT TAC CAA TTT TCC TCT GGC TCT TTT AAT TGG GAA AAA AGC CAG GAG         532
Cys Tyr Gln Phe Ser Ser Gly Ser Phe Asn Trp Glu Lys Ser Gln Glu
                155                 160                 165

AAC TGC TTG TCT TTG GAT GCC CAC TTG CTG AAG ATT AAT AGC ACA GAT         580
Asn Cys Leu Ser Leu Asp Ala His Leu Leu Lys Ile Asn Ser Thr Asp
            170                 175                 180

GAA CTG GAA TTC ATC CAG CAA ATG ATT GCC CAT TCC AGT TTC CCC TTC         628
Glu Leu Glu Phe Ile Gln Gln Met Ile Ala His Ser Ser Phe Pro Phe
            185                 190                 195

TGG ATG GGG TTG TCA ATG AGG AAA CCC AAT TAC TCG TGG CTT TGG GAA         676
Trp Met Gly Leu Ser Met Arg Lys Pro Asn Tyr Ser Trp Leu Trp Glu
200                 205                 210

GAT GGT ACT CCT TTG ACG CCC CAC TTG TTT AGA ATT CAG GGA GCT GTT         724
Asp Gly Thr Pro Leu Thr Pro His Leu Phe Arg Ile Gln Gly Ala Val
215                 220                 225                 230
```

```
TCC CGT ATG TAT CCT TCA GGG ACC TGT GCA TAT ATT CAA AGG GGA ACT        772
Ser Arg Met Tyr Pro Ser Gly Thr Cys Ala Tyr Ile Gln Arg Gly Thr
            235                 240                 245

GTT TTT GCT GAA AAC TGC ATT TTA ACT GCA TTC AGT ATA TGT CAA AAG        820
Val Phe Ala Glu Asn Cys Ile Leu Thr Ala Phe Ser Ile Cys Gln Lys
            250                 255                 260

AAG GCG AAT CTA TTG AGA GCA CAG TGA ATTTGAAGGA TCTGGAGGAA              867
Lys Ala Asn Leu Leu Arg Ala Gln  *
            265                 270

AAGAAGGAAA CCTTTGAATT CTCTTCTGGA ATTTAAGCTA TACTTCATCA CTTAGATGTA      927

AACCATTAGA GCCCAGGGAA ATGCCTGCTA CTGGTTGAGT GCAGAACTCC TTAGCAGAGA      987

CTGGCCCAGC TGCCTGGCAC CTTGATAGCA AAAGTTGCAA TTCCCTCTGT ATATTTTTCC     1047

CTAACTTGTT CCAAGTCCTC CCCTGCAGGA CTTCAGAGAA GTCAATTTTT CTGTTTCCAT     1107

TGTTTCTAAG AACTTGTTGC CTAACTCAAG GTCACAGCT TTTTCTCACT TTTGTCCTAT      1167

GCTTTCTTCT AGGCATTGTA GAGTTTTAGA TTTTACATGG AAATCTAGAA CTTATTTTAG     1227

ATTAATTTCT AAGTGATATA TGGATGTATG GAAGTTTTCT GTTTGTTTTT TGCTTGTGAG     1287

TATTCAATTG TTTTTGCAAC ATTTGCTGAA AAGACTATTC TTCCTTCACT ACATTGCCTT     1347

TGCACTGTTG TCAACAATTA TCCATACATG CCTGGCTCTA TTTCTGGATT TTCTATTCCT     1407

TTCCATTTAT TTATTTATTA TTCTTGGCTT ACAACATCAC CATGATATTT TGAATTCTAT     1467

GGTTCTTTAA TATATCTTGG AATCACATGG TAGTAGTTAT TCATTGTTGT TCTTTTTTAG     1527

AGTTGTTTGG TTAATCTATG CTTTTGTATT TCTGTCTTAA ATTGGCTTGT CCATTTCTAA     1587

AAAAACTTGA AATTTTGAAT TGCACTGAAT CCATACATAA ATTTAGGGAA AATTGAATTC     1647

TTAAAAATAC TGATTTGTTC AACTCATGAA AAAGGTGTAT TGCTCTATTT AGGTATTCCT     1707

TATTTTCTTT AAGCAATGCT TTTTAATGTT CTTTGTGTAG ATATTGTTAG ATTATCATCA     1767

TGTATTTCAC ATTATTTATG CTACTGTAGA TAGTATTGTT ATCATTGTT GTTCTTATTT      1827

TCAAAGTCTT CTGCTAGTAT GTAGAATTAT AATAAAGTTT GATATTAATA TTAAAAAAAA     1887

AAAAAAAAA                                                             1897

(2) INFORMATION FOR SEQ ID NO:2:

(i) SEQUENCE CHARACTERISTICS:
        (A) LENGTH:   270 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Val Asp Asp Pro Lys Gly Met Lys Asp Gln Leu Asp Gln Lys
 1               5                  10                  15

Pro Asn Gly Lys Thr Ala Lys Gly Phe Val Ser Ser Trp Arg Trp Tyr
            20                  25                  30

Pro Ala Ala Val Thr Leu Gly Val Leu Cys Leu Gly Leu Leu Val Thr
            35                  40                  45

Val Ile Leu Leu Ile Leu Gln Leu Ser Gln Val Ser Asp Leu Ile Lys
            50                  55                  60

Lys Gln Gln Ala Asn Ile Thr His Gln Glu Asp Ile Leu Glu Gly Gln
 65                  70                  75                  80

Ile Leu Ala Gln Arg Arg Ser Glu Lys Ser Ala Gln Glu Ser Gln Lys
            85                  90                  95
```

```
Glu Leu Lys Glu Met Ile Glu Thr Leu Ala His Lys Leu Asp Glu Lys
            100                 105                 110

Ser Lys Lys Leu Met Glu Leu His Arg Gln Asn Leu Asn Leu Gln Glu
        115                 120                 125

Val Leu Lys Glu Ala Ala Asn Tyr Ser Gly Pro Cys Pro Gln Asp Trp
130                 135                 140

Leu Trp His Glu Glu Asn Cys Tyr Gln Phe Ser Ser Gly Ser Phe Asn
145                 150                 155                 160

Trp Glu Lys Ser Gln Glu Asn Cys Leu Ser Leu Asp Ala His Leu Leu
                165                 170                 175

Lys Ile Asn Ser Thr Asp Glu Leu Glu Phe Ile Gln Gln Met Ile Ala
                180                 185                 190

His Ser Ser Phe Pro Phe Trp Met Gly Leu Ser Met Arg Lys Pro Asn
                195                 200                 205

Tyr Ser Trp Leu Trp Glu Asp Gly Thr Pro Leu Thr Pro His Leu Phe
        210                 215                 220

Arg Ile Gln Gly Ala Val Ser Arg Met Tyr Pro Ser Gly Thr Cys Ala
225                 230                 235                 240

Tyr Ile Gln Arg Gly Thr Val Phe Ala Glu Asn Cys Ile Leu Thr Ala
                245                 250                 255

Phe Ser Ile Cys Gln Lys Lys Ala Asn Leu Leu Arg Ala Gln
                260                 265                 270

(2) INFORMATION FOR SEQ ID NO:3:

(i) SEQUENCE CHARACTERISTICS:
        (A) LENGTH: 1906 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Bos taurus
        (F) TISSUE TYPE: Vascular endothelial cells (vii) IMMEDIATE SOURCE:
        (A) LIBRARY: Bovine aortic edothelial cells cDNA
        (B) CLONE: pBLOX-1

(ix) FEATURE:
        (A) NAME/KEY: polyA_site
        (B) LOCATION: 1889..1906

(ix) FEATURE:
        (A) NAME/KEY: misc_RNA
        (B) LOCATION: 1864..1873
        (D) OTHER INFORMATION: /function= "PolyA Signal"

(ix) FEATURE:
        (A) NAME/KEY: 5'UTR
        (B) LOCATION: 1..34

(ix) FEATURE:
        (A) NAME/KEY: 3'UTR
        (B) LOCATION: 857..1906

(ix) FEATURE:
        (A) NAME/KEY: CDS
        (B) LOCATION: 35..856

(xi) SEQUENCE DESCRIPTION: SEQ ID NO:3:
```

```
GCTTCACTCT CTCATTCTTG GAATACATTT GAAA ATG ACT GTT GAT GAC CCC                    52
                                     Met Thr Val Asp Asp Pro
                                      1               5

AAG GGT ATG AAA GAT CAA CTT GAT CAG AAG CCA AAT GGC AAG ACA GCA                 100
Lys Gly Met Lys Asp Gln Leu Asp Gln Lys Pro Asn Gly Lys Thr Ala
             10              15              20

AAA GGT ACT ACA GGT TTT GTT TCC TCT TGG AGG TGG TAC CCT GCT GCT                 148
Lys Gly Thr Thr Gly Phe Val Ser Ser Trp Arg Trp Tyr Pro Ala Ala
         25              30              35

GTG ACT CTA GGG GTC CTT TGT CTG GGA TTA CTG GTG ACT GTT ATA TTG                 196
Val Thr Leu Gly Val Leu Cys Leu Gly Leu Leu Val Thr Val Ile Leu
     40              45              50

TTG ATA CTG CAA TTA TCC CAG GTC TCT GAT CTC ATA AAG AAA CAG CAA                 244
Leu Ile Leu Gln Leu Ser Gln Val Ser Asp Leu Ile Lys Lys Gln Gln
 55              60              65              70

GCA AAT ATT ACT CAC CAG GAA GAT ATC CTG GAG GGA CAG ATT TTA GCC                 292
Ala Asn Ile Thr His Gln Glu Asp Ile Leu Glu Gly Gln Ile Leu Ala
                 75              80              85

CAG CGC CGA TCA GAA AAA TCT GCC CAG GAG TCA CAG AAG GAA CTC AAA                 340
Gln Arg Arg Ser Glu Lys Ser Ala Gln Glu Ser Gln Lys Glu Leu Lys
             90              95             100

GAA ATG ATA GAA ACC CTT GCC CAC AAG CTG GAT GAG AAA TCC AAG AAA                 388
Glu Met Ile Glu Thr Leu Ala His Lys Leu Asp Glu Lys Ser Lys Lys
        105             110             115

CTA ATG GAA CTT CAC CGC CAG AAC CTG AAT CTC CAA GAA GTT CTG AAA                 436
Leu Met Glu Leu His Arg Gln Asn Leu Asn Leu Gln Glu Val Leu Lys
    120             125             130

GAG GCA GCA AAC TAT TCA GGT CCT TGT CCC CAA GAC TGG CTC TGG CAT                 484
Glu Ala Ala Asn Tyr Ser Gly Pro Cys Pro Gln Asp Trp Leu Trp His
135             140             145             150

GAA GAA AAC TGT TAC CAA TTT TCC TCT GGC TCT TTT AAT TGG GAA AAA                 532
Glu Glu Asn Cys Tyr Gln Phe Ser Ser Gly Ser Phe Asn Trp Glu Lys
            155             160             165

AGC CAG GAG AAC TGC TTG TCT TTG GAT GCC CAC TTG CTG AAG ATT AAT                 580
Ser Gln Glu Asn Cys Leu Ser Leu Asp Ala His Leu Leu Lys Ile Asn
        170             175             180

AGC ACA GAT GAA CTG GAA TTC ATC CAG CAA ATG ATT GCC CAT TCC AGT                 628
Ser Thr Asp Glu Leu Glu Phe Ile Gln Gln Met Ile Ala His Ser Ser
    185             190             195

TTC CCC TTC TGG ATG GGG TTG TCA ATG AGG AAA CCC AAT TAC TCG TGG                 676
Phe Pro Phe Trp Met Gly Leu Ser Met Arg Lys Pro Asn Tyr Ser Trp
200             205             210

CTT TGG GAA GAT GGT ACT CCT TTG ACG CCC CAC TTG TTT AGA ATT CAG                 724
Leu Trp Glu Asp Gly Thr Pro Leu Thr Pro His Leu Phe Arg Ile Gln
215             220             225             230

GGA GCT GTT TCC CGT ATG TAT CCT TCA GGG ACC TGT GCA TAT ATT CAA                 772
Gly Ala Val Ser Arg Met Tyr Pro Ser Gly Thr Cys Ala Tyr Ile Gln
            235             240             245

AGG GGA ACT GTT TTT GCT GAA AAC TGC ATT TTA ACT GCA TTC AGT ATA                 820
Arg Gly Thr Val Phe Ala Glu Asn Cys Ile Leu Thr Ala Phe Ser Ile
        250             255             260

TGT CAA AAG AAG GCG AAT CTA TTG AGA GCA CAG TGA ATTTGAAGGA                      866
Cys Gln Lys Lys Ala Asn Leu Leu Arg Ala Gln *
    265             270

TCTGGAGGAA AAGAAGGAAA CCTTTGAATT CTCTTCTGGA ATTTAAGCTA TACTTCATCA               926

CTTAGATGTA AACCATTAGA GCCCAGGGAA ATGCCTGCTA CTGGTTGAGT GCAGAACTCC               986

TTAGCAGAGA CTGGCCCAGC TGCCTGGCAC CTTGATAGCA AAAGTTGCAA TTCCCTCTGT              1046

ATATTTTTCC CTAACTTGTT CCAAGTCCTC CCCTGCAGGA CTTCAGAGAA GTCAATTTTT              1106
```

```
CTGTTTCCAT TGTTTCTAAG AACTTGTTGC CTAACTCAAG GTCACAGCAT TTTTCTCACT    1166

TTTGTCCTAT GCTTTCTTCT AGGCATTGTA GAGTTTTAGA TTTTACATGG AAATCTAGAA    1226

CTTATTTTAG ATTAATTTCT AAGTGATATA TGGATGTATG GAAGTTTTCT GTTTGTTTTT    1286

TGCTTGTGAG TATTCAATTG TTTTTGCAAC ATTTGCTGAA AAGACTATTC TTCCTTCACT    1346

ACATTGCCTT TGCACTGTTG TCAACAATTA TCCATACATG CCTGGCTCTA TTTCTGGATT    1406

TTCTATTCCT TTCCATTTAT TTATTTATTA TTCTTGGCTT ACAACATCAC CATGATATTT    1466

TGAATTCTAT GGTTCTTTAA TATATCTTGG AATCACATGG TAGTAGTTAT TCATTGTTGT    1526

TCTTTTTTAG AGTTGTTTGG TTAATCTATG CTTTTGTATT TCTGTCTTAA ATTGGCTTGT    1586

CCATTTCTAA AAAAACTTGA AATTTTGAAT TGCACTGAAT CCATACATAA ATTTAGGGAA    1646

AATTGAATTC TTAAAAATAC TGATTTGTTC AACTCATGAA AAAGGTGTAT TGCTCTATTT    1706

AGGTATTCCT TATTTTCTTT AAGCAATGCT TTTTAATGTT CTTTGTGTAG ATATTGTTAG    1766

ATTATCATCA TGTATTTCAC ATTATTTATG CTACTGTAGA TAGTATTGTT ATCATTTGTT    1826

GTTCTTATTT TCAAAGTCTT CTGCTAGTAT GTAGAATTAT AATAAAGTTT GATATTAATA    1886

TTAAAAAAAA AAAAAAAAA                                                 1906
```

(2) INFORMATION FOR SEQ ID NO:4:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Val Asp Asp Pro Lys Gly Met Lys Asp Gln Leu Asp Gln Lys
 1               5                  10                  15

Pro Asn Gly Lys Thr Ala Lys Gly Thr Thr Gly Phe Val Ser Ser Trp
                20                  25                  30

Arg Trp Tyr Pro Ala Ala Val Thr Leu Gly Val Leu Cys Leu Gly Leu
            35                  40                  45

Leu Val Thr Val Ile Leu Leu Ile Leu Gln Leu Ser Gln Val Ser Asp
    50                  55                  60

Leu Ile Lys Lys Gln Gln Ala Asn Ile Thr His Gln Glu Asp Ile Leu
65                  70                  75                  80

Glu Gly Gln Ile Leu Ala Gln Arg Arg Ser Glu Lys Ser Ala Gln Glu
                85                  90                  95

Ser Gln Lys Glu Leu Lys Glu Met Ile Glu Thr Leu Ala His Lys Leu
            100                 105                 110

Asp Glu Lys Ser Lys Lys Leu Met Glu Leu His Arg Gln Asn Leu Asn
        115                 120                 125

Leu Gln Glu Val Leu Lys Glu Ala Ala Asn Tyr Ser Gly Pro Cys Pro
    130                 135                 140

Gln Asp Trp Leu Trp His Glu Glu Asn Cys Tyr Gln Phe Ser Ser Gly
145                 150                 155                 160

Ser Phe Asn Trp Glu Lys Ser Gln Glu Asn Cys Leu Ser Leu Asp Ala
                165                 170                 175

His Leu Leu Lys Ile Asn Ser Thr Asp Glu Leu Glu Phe Ile Gln Gln
            180                 185                 190

Met Ile Ala His Ser Ser Phe Pro Phe Trp Met Gly Leu Ser Met Arg
        195                 200                 205
```

```
Lys Pro Asn Tyr Ser Trp Leu Trp Glu Asp Gly Thr Pro Leu Thr Pro
    210                 215                 220
His Leu Phe Arg Ile Gln Gly Ala Val Ser Arg Met Tyr Pro Ser Gly
225                 230                 235                 240
Thr Cys Ala Tyr Ile Gln Arg Gly Thr Val Phe Ala Glu Asn Cys Ile
                245                 250                 255
Leu Thr Ala Phe Ser Ile Cys Gln Lys Lys Ala Asn Leu Leu Arg Ala
            260                 265                 270
Gln
```

(2) INFORMATION FOR SEQ ID NO:5:

(i) SEQUENCE CHARACTERISTICS:
        (A) LENGTH: 1318 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo Sapiens
        (F) TISSUE TYPE: Lung, placenta (vii) IMMEDIATE SOURCE:
        (A) LIBRARY: Human lung cDNA
        (B) CLONE: lambdahLOX-1

(ix) FEATURE:
        (A) NAME/KEY: 5'UTR
        (B) LOCATION: 66..125

(ix) FEATURE:
        (A) NAME/KEY: 3'UTR
        (B) LOCATION: 949..1309

(ix) FEATURE:
        (A) NAME/KEY: CDS
        (B) LOCATION: 127..948

(xi) SEQUENCE DESCRIPTION: SEQ ID NO:5:

```
GGGGCCGCAC TAGTGATTCT GGTTCGGCCC ACCTCTGAAG GTTCCAGAAT CGATAGTGAA      60

TTCGTGATTT TAGTTTGTTG AAGTTCGTGA CTGCTTCACT CTCTCATTCT TAGCTTGAAT     120

TTGGAA ATG ACT TTT GAT GAC CTA AAG ATC CAG ACT GTG AAG GAC CAG        168
       Met Thr Phe Asp Asp Leu Lys Ile Gln Thr Val Lys Asp Gln
       1               5                  10

CCT GAT GAG AAG TCA AAT GGA AAA AAA GCT AAA GGT CTT CAG TTT CTT       216
Pro Asp Glu Lys Ser Asn Gly Lys Lys Ala Lys Gly Leu Gln Phe Leu
15                  20                  25                  30

TAC TCT CCA TGG TGG TGC CTG GCT GCT GCG ACT CTA GGG GTC CTT TGC       264
Tyr Ser Pro Trp Trp Cys Leu Ala Ala Ala Thr Leu Gly Val Leu Cys
                35                  40                  45

CTG GGA TTA GTA GTG ACC ATT ATG GTG CTG GGC ATG CAA TTA TCC CAG       312
Leu Gly Leu Val Val Thr Ile Met Val Leu Gly Met Gln Leu Ser Gln
            50                  55                  60

GTG TCT GAC CTC CTA ACA CAA GAG CAA GCA AAC CTA ACT CAC CAG AAA       360
Val Ser Asp Leu Leu Thr Gln Glu Gln Ala Asn Leu Thr His Gln Lys
        65                  70                  75

AAG AAA CTG GAG GGA CAG ATC TCA GCC CGG CAA CAA GCA GAA GAA GCT       408
Lys Lys Leu Glu Gly Gln Ile Ser Ala Arg Gln Gln Ala Glu Glu Ala
    80                  85                  90
```

```
TCA CAG GAG TCA GAA AAC GAA CTC AAG GAA ATG ATA GAA ACC CTT GCT      456
Ser Gln Glu Ser Glu Asn Glu Leu Lys Glu Met Ile Glu Thr Leu Ala
 95                 100                 105                 110

CGG AAG CTG AAT GAG AAA TCC AAA GAG CAA ATG GAA CTT CAC CAC CAG      504
Arg Lys Leu Asn Glu Lys Ser Lys Glu Gln Met Glu Leu His His Gln
                115                 120                 125

AAT CTG AAT CTC CAA GAA ACA CTG AAG AGA GTA GCA AAT TGT TCA GCT      552
Asn Leu Asn Leu Gln Glu Thr Leu Lys Arg Val Ala Asn Cys Ser Ala
            130                 135                 140

CCT TGT CCG CAA GAC TGG ATC TGG CAT GGA GAA AAC TGT TAC CTA TTT      600
Pro Cys Pro Gln Asp Trp Ile Trp His Gly Glu Asn Cys Tyr Leu Phe
        145                 150                 155

TCC TCG GGC TCA TTT AAC TGG GAA AAG AGC CAA GAG AAG TGC TTG TCT      648
Ser Ser Gly Ser Phe Asn Trp Glu Lys Ser Gln Glu Lys Cys Leu Ser
    160                 165                 170

TTG GAT GCC AAG TTG CTG AAA ATT AAT AGC ACA GCT GAT CTG GAC TTC      696
Leu Asp Ala Lys Leu Leu Lys Ile Asn Ser Thr Ala Asp Leu Asp Phe
175                 180                 185                 190

ATC CAG CAA GCA ATT TCC TAT TCC AGT TTT CCA TTC TGG ATG GGG CTG      744
Ile Gln Gln Ala Ile Ser Tyr Ser Ser Phe Pro Phe Trp Met Gly Leu
                195                 200                 205

TCT CGG AGG AAC CCC AGC TAC CCA TGG CTC TGG GAG GAC GGT TCT CCT      792
Ser Arg Arg Asn Pro Ser Tyr Pro Trp Leu Trp Glu Asp Gly Ser Pro
            210                 215                 220

TTG ATG CCC CAC TTA TTT AGA GTC CGA GGC GCT GTC TCC CAG ACA TAC      840
Leu Met Pro His Leu Phe Arg Val Arg Gly Ala Val Ser Gln Thr Tyr
        225                 230                 235

CCT TCA GGT ACC TGT GCA TAT ATA CAA CGA GGA GCT GTT TAT GCG GAA      888
Pro Ser Gly Thr Cys Ala Tyr Ile Gln Arg Gly Ala Val Tyr Ala Glu
    240                 245                 250

AAC TGC ATT TTA GCT GCC TTC AGT ATA TGT CAG AAG AAG GCA AAC CTA      936
Asn Cys Ile Leu Ala Ala Phe Ser Ile Cys Gln Lys Lys Ala Asn Leu
255                 260                 265                 270

AGA GCA CAG TGA ATTTGAAGGC TCTGGAAGAA AAGAAAAAAG TCTTTGAGTT          988
Arg Ala Gln  *

TTATTCTGGA ATTTAAGCTA TTCTTTGTCA CTTGGGTGCC AAACATGAGA GCCCAGAAAA   1048

CTGTCATTTA GCTGGCTGCA GAACTCCTTT GCAGAAACTG GGGTTCCAGG TGCCTGGCAC   1108

CTTTATGTCA ACATTTTTGA TTCTAGCTAT CTGTATTATT TCACCTAGCT TGTCCCAAGC   1168

TTCCCTGCCA GCCTGAAGTC CATTTTCCCC TTTTTATTTT AAAATTTGAC TCCTCTTCAA   1228

GCTTGAAAAC CCTCTGAACT CAGTCTTCTT TACCTCATTA TCACCTTCCC CTCACACTCC   1288

TAAAATTGCA TGAAAGACAG ACCGGAATTC                                    1318

(2) INFORMATION FOR SEQ ID NO:6:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:6:

Met Thr Phe Asp Asp Leu Lys Ile Gln Thr Val Lys Asp Gln Pro Asp
  1               5                  10                  15

Glu Lys Ser Asn Gly Lys Lys Ala Lys Gly Leu Gln Phe Leu Tyr Ser
                 20                  25                  30

Pro Trp Trp Cys Leu Ala Ala Ala Thr Leu Gly Val Leu Cys Leu Gly
         35                  40                  45
```

```
Leu Val Val Thr Ile Met Val Leu Gly Met Gln Leu Ser Gln Val Ser
    50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Ala Glu Gly Ala Ser Gln
                85                  90                  95

Glu Ser Glu Asn Glu Leu Lys Glu Met Ile Glu Thr Leu Ala Arg Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
        195                 200                 205

Arg Asn Pro Ser Tyr Pro Trp Leu Trp Glu Asp Gly Ser Pro Leu Met
    210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Lys Ala Asn Leu Arg Ala
            260                 265                 270

Gln
```

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (xi) SEQUENCE DESCRIPTION: SEQ ID NO:7:

GCGGATCCTG TGCTCTCAAT AGATTCGC                               28

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (xi) SEQUENCE DESCRIPTION: SEQ ID NO:8:

GGGGATCCTG ATCTCATAAA GAAACAG                                27

RECOMBINANT PRODUCTION OF HUMAN AND BOVINE RECEPTORS FOR MODIFIED LOW-DENSITY LIPOPROTEIN

FIELD OF THE INVENTION

The present invention relates to a mammalian receptor for modified low-density lipoprotein (LDL), and in more detail relates to a mammalian vascular endothelial receptor for modified low-density lipoprotein.

BACKGROUND OF THE INVENTION

Vascular endothelial dysfunction has been pointed out as an important index in the early stages of progressive atherosclerosis. The vascular endothelial cell releases many sorts of humoral factors to keep circulatory homeostasis. The vascular endothelial function is inhibited by physical stimuli or various substances including the most important factor, oxidized low-density lipoprotein, which is a kind of modified low-density lipoproteins. For example, the vascular endothelial cell releases nitrogen monoxide as a vasohypotonic factor to adjust vascular tonus. The release of nitrogen monoxide is inhibited by the oxidized low-density lipoprotein.

It has been known that macrophages or vascular endothelial cells internalize the modified low-density lipoprotein through a receptor other than receptors for low-density lipoprotein. The macrophages internalize the modified low-density lipoprotein through scavenger receptors, which have already been structurally analyzed (cf., PCT Patent Japanese Publication Nos. 6(1994)-500765 and 6(1994)-508604, and Japanese Patent Provisional Publication No. 3(1991)-290184). The macrophages are then changed to foam cells, which are specific in arteriosclerotic focus. Since the macrophage scavenger receptors are not found in vascular endothelial cells, it has been anticipated that receptors of another structure are present in the vascular endothelial cells (cf., Hidenori Arai, Toru Kita, Oxidized LDL, Metabolism 28/4, 1991).

For the reasons mentioned above, it is necessary to analyze the structure of an endothelial receptor for modified low-density lipoprotein, namely the amino acid sequence of the receptor. However, the structure and the amino acid sequence have not yet been elucidated.

DISCLOSURE OF THE INVENTION

According to study of the present inventors, the structure of the vascular endothelial receptor for modified low-density lipoprotein is now elucidated. The amino acid sequences of the vascular endothelial receptor for modified low-density lipoprotein are set forth in SEQ ID NOS: 2, 4 and 6.

There is provided by the present invention a DNA sequence essentially encoding a mammalian vascular endothelial receptor for modified low-density lipoprotein.

The DNA sequence can be cDNA clones derived from the open reading frame of a gene corresponding to a native mammalian vascular endothelial receptor for modified low-density lipoprotein. The DNA sequence can also be a sequence which is capable of hybridization to the above-mentioned cDNA clones and encodes a biologically active mammalian vascular endothelial receptor for modified low-density lipoprotein. Further, the sequence can be degenerate as a result of the genetic code to the above-mentioned DNA sequences. The degenerate encodes the same biologically active receptor for modified low-density lipoprotein. Therefore, the present invention provides a DNA sequence set forth in SEQ ID NO: 1, 3 or 5(DNA having the sequence) or an analogue thereof, which corresponds to the region encoding a mammalian vascular endothelial receptor for modified low-density lipoprotein.

The present invention also provides a CDNA clone having a DNA sequence set forth in SEQ ID NO: 1, 3 or 5 or an analogue thereof, which corresponds to the region encoding a mammalian vascular endothelial receptor for modified low-density lipoprotein.

The present invention further provides a DNA sequence which is capable of hybridization to a cDNA clone of a DNA sequence set forth in SEQ ID NO: 1, 3 or 5 (DNA having the sequence) in 20% (v/v) formamide at 42° C., and encodes a protein of a mammalian vascular endothelial cell, said protein having a function of binding a modified low-density lipoprotein (namely a receptor thereof).

The present invention furthermore provides a DNA sequence which is degenerate as a result of the genetic code to a DNA sequence set forth in SEQ ID NO: 1, 3 or 5 (DNA having the sequence), and encodes a protein of a mammalian vascular endothelial cell, said protein having a function of binding a modified low-density lipoprotein (namely a receptor thereof).

Moreover, the present invention relates to an antibody of a receptor for modified low-density lipoprotein corresponding to a DNA sequence set forth in SEQ ID NO: 1, 3 or 5 or an analogue thereof (or a receptor for modified low-density lipoprotein containing an amino acid sequence set forth in SEQ ID NOS: 2, 4 or 6 or an analogue thereof).

The DNA sequence of the present invention can be integrated into an expression vector. Therefore, the present invention further provides a process for the production of mammalian vascular endothelial receptor for modified lowensity lipoprotein or an analogue thereof, which comprises nserting the recombinant expression vector into a host cell and culturing the cell under expression promoting conditions.

The invention furthermore provides a protein composition containing a biologically active mammalian vascular endothelial receptor for modified low-density lipoprotein or an analogue thereof which is produced as mentioned above.

The obtained protein composition containing a biologically active mammalian vascular endothelial receptor for modified low-density lipoprotein or an analogue thereof is effective in an assay of the mammalian modified low-density lipoprotein. The composition can also be used in preparation of an antibody to the vascular endothelial receptor for modified low-density lipoprotein. The antibody can be used in diagnosis.

It is apparent from the above-described biological activities of the modified low-density lipoprotein and the receptor thereof that an agent containing an antibody to the vascular endothelial receptor for modified low-density lipoprotein is effective in diagnosis of atherosclerosis.

In the present specification, the term "receptor for modified low-density lipoprotein" means proteins which are capable of binding modified low-density lipoprotein molecules and, in their native configuration as mammalian plasma membrane proteins, presumably play a role in transducing the signal provided by a modified low-density lipoprotein to a vascular endothelial cell. In the specification, the term includes analogues of native proteins with an activity of binding a modified low-density lipoprotein or a signal transducing activity.

The term "subtype of a receptor for modified low-density lipoprotein" means molecules of a receptor for modified low-density lipoprotein which show different pharmacological potency rank orders, namely different affinities or selectivities for various isopeptides of modified low-density lipoprotein, such as oxidized low-density lipoprotein or acetylated low-density lipoprotein.

The term "essentially" used in the expression "a DNA sequence essentially encoding a receptor for modified low-density lipoprotein" or the like means that a particular subject sequence, for example, a mutant sequence, varies from a reference sequence by one or more substitutions, deletions, or additions, the net effect of which does not result in an adverse functional dissimilarity between subject sequence and reference sequence set forth in the SEQ ID NO: 1, 3 or 5.

In more detail, the sequence can be modified so long as a protein corresponding to the sequence has a biological activity (described below), namely an activity of binding modified low-density lipoprotein. Therefore, the region encoding a portion of binding modified low-density lipoprotein should be the same as the reference sequence set forth in the SEQ ID NO: 1, 3 or 5 except for variation due to code degeneracy and substitution of an amino acid to an analogous amino acid. The other region merely requires at least 30% (preferably at least 50%, and more preferably at least 80%) similarity in the sequence.

The above-mentioned substitution to an analogous amino acid means amino acid substitution in a group where the natural amino acids are classified into the following eight groups.

(1) Monoaminomonocarboxylic acid Gly, Ala, Val, Leu, Ile
(2) Oxyamino acid Ser, Thr
(3) Sulfur-containing amino acid Cys, Met
(4) Monoaminodicarboxylic acid Asp, Glu
(5) Diaminomonocarboxylic acid Lys, Arg
(6) Aromatic amino acid Phe, Tyr
(7) Heterocyclic amino acid His, Trp, Pro
(8) Amide amino acid Asn, Gln For purposes of determining similarity, truncation or internal deletions of the reference sequence should be disregarded. Sequences having lesser degrees of similarity, comparable biological activity, and equivalent expression characteristics are considered to be essential equivalents.

The term "biologically active" used as a characteristic of a receptor for modified low-density lipoprotein means either that a particular molecule has sufficient amino acid sequence similarity with the embodiments of the present invention having an activity of binding modified low-density lipoprotein, or that a particular molecule has sufficient amino acid sequences similarity to the receptor for modified low-density lipoprotein to be capable of transmitting stimulus of the modified low-density lipoprotein to cell as a component of hybrid receptor constructs.

In more detail, the affinity (dissociation constant) of a particular molecule for standard oxidized low-density lipoprotein is not more than 1 $\mu$M. In the present invention, the affinity preferably is not more than 0.1 $\mu$M, and more preferably is not more than 0.01 $\mu$M.

The term "biologically active" also means that a particular molecule has a function of accelerating internalization of modified low-density lipoprotein into vascular endothelial cells.

The term "DNA sequence" means a DNA polymer, in the form of a separate fragment or as a component of larger DNA constructs. The DNA constructs are derived from DNA isolated at least once in essentially pure form (free of contaminating endogenous materials) and in a quantity or concentration enabling identification, manipulation, and recovery of the sequence and its component nucleotides sequences by standard biochemical methods, for example, using a cloning vector. The DNA sequences are preferably provided in the form of an open reading frame uninterrupted by internal nontranslated sequences, or introns, which are typically present in eukaryotic genes. However, genomic DNA containing the relevant sequences can also be used. Sequences of non-translated DNA may be present 5' or 3' from the open reading frame. The non-translated DNA does not interfere with manipulation or expression of the coding regions.

The term "recombinant expression vector" means a plasmid comprising a transcriptional unit. The unit comprises (a) a genetic element or elements having a regulatory role in gene expression, for example, promoters or enhancers, (b) a structural or coding sequence which is transcribed into MRNA and translated into protein, and (c) appropriate transcription and translation initiation and termination sequences. Structural elements used in yeast expression systems preferably include a leader sequence enabling extracellular secretion of translated protein by a host cell. In the case that a recombinant protein is expressed without a leader or transport sequence, it may include an N-terminal methionine residue. This residue may optionally be cleaved from the expressed recombinant protein to provide a final product.

PREFERRED EMBODIMENTS OF THE INVENTION

Figure 1:
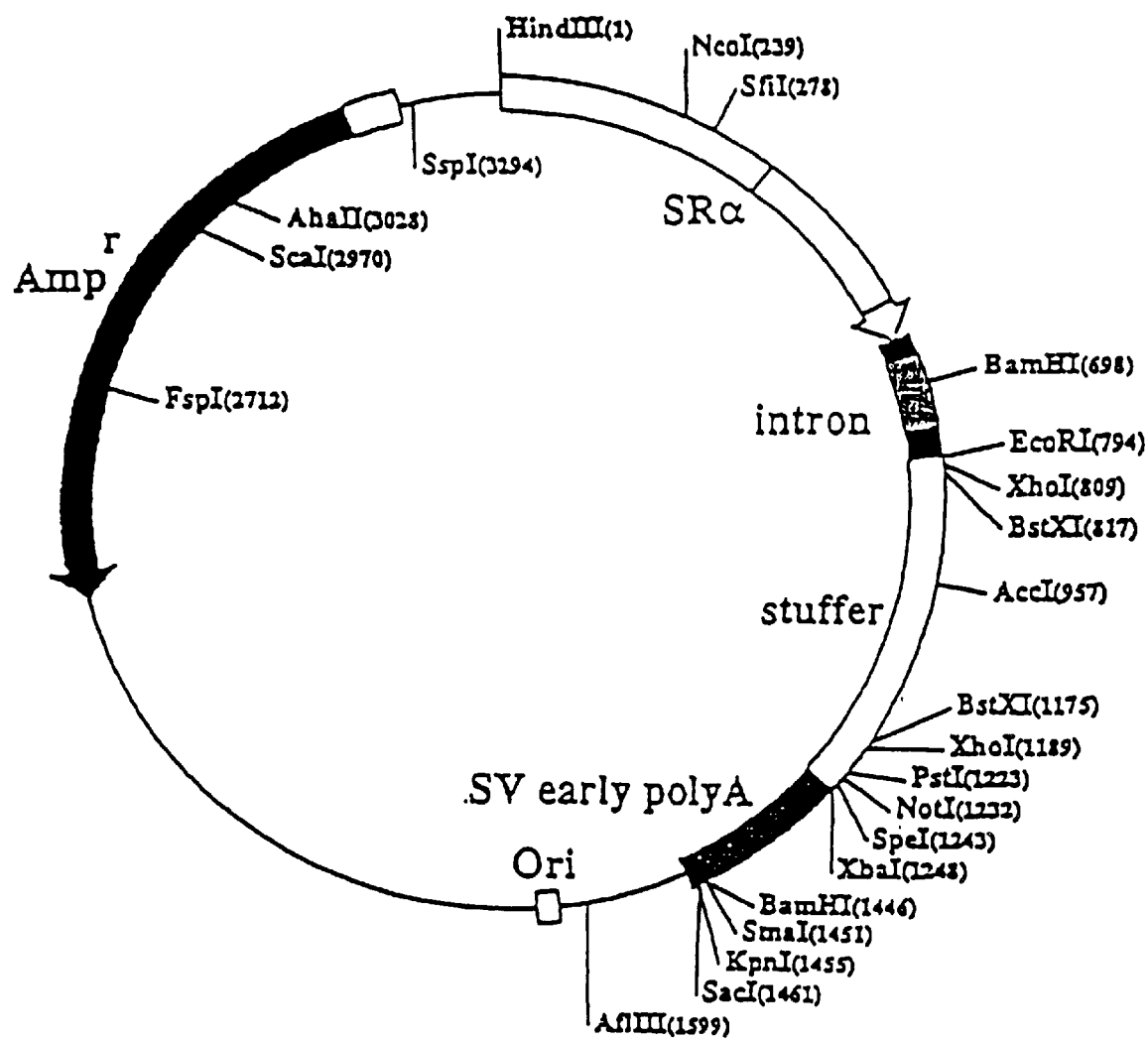
FIG. 1 schematically illustrates a high expression lasmid vector, pME18S used in Example 1.

Next, isolation of cDNA encoding the receptor for modified low-density lipoprotein and determination of the DNA sequence are described below.

A cDNA library was prepared by a reverse transcription of poly(A)$^+$ RNA, which was isolated from cultured bovine aortic endothelial cells. A DNA sequence encoding a bovine receptor for modified low-density lipoprotein was isolated from the cDNA library. The library was screened by direct expression of MRNA from DNA fragments accumulated in monkey COS-7 cells using a mammalian expression vector (pME18S). The vector contains regulatory sequences derived from SV40, human T lymphocyte leukemic virus type I. Transfected COS-7 cells were incubated in a culture medium containing DiI (1,1'-di-octadecyl-3,3,3',3'-tetramethylindocarbocyanine perchlorate)-labeled oxidized low-density lipoproteins. The cells were washed to remove free DiI-labeled oxidized low-density lipoproteins. The cells were subjected to tripsinization to suspend the cells. The cells were treated in FACS (fluorescence-activated cell sorter) to measure fluorescence of DiI and to recover cells showing high fluorescent intensity. Plasmid was extracted from the transfected cells, and E. coli was transformed with the plasmids. Plasmids were purified and the above-mentioned procedures were repeated. The procedures were repeated four times to synthesize monoclonal surface protein having an activity of binding modified low-density lipoprotein. The clone was isolated, and the insertion fragment sequence as examined to determine cDNA sequence of a bovine receptor for modified low-density lipoprotein.

COS-7 cells were transfected with isolated cDNA clone to express the gene. As a result, the cells obtained a specific binding activity to oxidized low-density lipoprotein. The modified low-density lipoprotein is internalized into the cells. Further, the cells do not have an activity of binding native (not modified) low-density lipoprotein. Accordingly, the receptor is considered specific to modified low-density lipoprotein.

The above-determined DNA sequence encoding the receptor for modified low-density lipoprotein are set forth in Sequence Nos. 1 and 3. The corresponding sequences are set forth in SEQ ID NOS: 2 and 4.

The DNA sequence and the amino acid sequence are described below.

As is shown in the SEQ ID NOS: 2 and 4, the receptor for modified low-density lipoprotein has at least two sub-types. The SEQ ID NO: 4 is the same as the SEQ ID NO: 2, except that three amino acids (Thr Thr Gly) are inserted after the 24th amino acid (Gly) of the SEQ ID NO: 2. In the present specification, the sequence is described referring to the SEQ ID NO: 2 unless otherwise specified.

There is an open reading frame of 810bp encoding 270 amino acid residues from the first ATG (initiation codon encoding methionine) to the stop codon of TGA (811–813). The 3' nontranslated region in the mRNA of the receptor for modified low-density lipoprotein encoded by this cDNA contains seven AUUUA sequences which unstabilize mRNA. This is analogous to transiently expressed cytokine or growth factor.

The encoded polypeptide contains a stretch of 26 hydrophobic amino acid residues (amino acid Nos. 31–56 in the SEQ ID NO: 2 and amino acid Nos. 34–59 in the SEQ ID NO: 4), which are likely to represent a transmembrane domain. The C-terminal region after the putative transmembrane domain contains four potential glycosylation sites (amino acid Nos. 69, 135, 179 and 208 in the SEQ ID NO: 1 and amino acid Nos. 72, 138, 182 and 211 in the SEQ ID NO: 4).

Further, a cDNA library was prepared by a reverse transcription of poly(A)+ RNA, which was extracted from human lung. A DNA sequence encoding the human receptor for modified low-density lipoprotein was isolated from the cDNA library. The library was screened according to a plaque hybridization method using XhoI/PstI fragments of pBMLR1, which was labeled with [α-32P]dCTP. The hybridization was conducted at 55° C. in 50 mM Tris-HCl (pH 7.5), 1M NaCl, 1% SDS, 0.2 g/l Yeast tRNA. After the hybrid was washed three times with 2xSSC/0.1% SDS for 15 minutes, positive clone was identified by an autoradiography. The clone was isolated, and the insertion fragment sequence was examined to determine cDNA sequence of a human receptor for modified low-density lipoprotein. The sequence seemed a part of a domain encoding the protein. Therefore, cDNA encoding the whole protein was obtained from cDNA library prepared by a reverse transcription of poly(A)+ RNA, which was extracted from human placenta. The procedures were conducted according to 5'-RACE (rapid amplification of cDNA end) method by using the partial sequence.

The SEQ ID NO: 5 shows the DNA sequence of the human receptor for modified low-density lipoprotein SEQ ID NO: 6 shows the amino acid sequence of the human receptor for modified low-density lipoprotein.

The human sequence as well as the bovine sequence has an open reading frame of 810 bp encoding 270 amino acid residues from the first ATG (initiation codon encoding methionine) to the stop codon of TGA (811–813).

The polypeptide encoded by the cDNA contains a stretch of 27 hydrophobic amino acid residues in analogy with bovine sequence, which are likely to represent a transmembrane domain. The C-terminal region after the putative transmembrane domain contains four potential glycosylation sites (amino acid Nos. 69, 135, 179 and 206).

Each of the bovine and human amino acid sequences has the structure of C-type lectin in an extracellular domain. The domain (amino acid Nos. 140–270) is considered to have an activity of binding modified low-density lipoprotein. Therefore, the peptide having the partial sequence of the amino acid Nos. 140–270 is also considered to have an activity of binding modified low-density lipoprotein.

The present invention provides the above-described DNA sequence encoding the receptor for modified low-density lipoprotein and the DNA sequence encoding the partial sequence of the amino acid Nos. 140–270. The DNA sequence is preferably provided in a form which is capable of being expressed in a recombinant transcriptional unit under the control of mammalian, microbial, viral transcriptional or translational control elements. For example, a sequence to be expressed in a microorganism will contain no introns. In a preferred embodiment, the DNA sequence comprises at least one, but optionally more than one sequence component derived from a cDNA sequence or copy thereof.

The sequences may be linked or flanked by DNA sequence prepared by assembly of synthetic oligonucleotides. However, synthetic genes assembled exclusively from oligonucleotides could be constructed using the sequence information provided herein. A representative sequence contains those essentially identical to the nucleotide sequences set forth in the SEQ ID NOS: 1, 3 to 3. The coding sequences may include codons encoding one or more additional amino acids located at the N-terminus, for example, an N-terminal ATG codons specifying methionine linked with reading frame in the nucleotide sequence. Due to code degeneracy, there can be considerable variation in nucleotide sequences encoding the same amino acid sequence. Other embodiments include sequences capable of hybridizing to the representative sequence under moderately stringent conditions (420° C., 20% (v/v) formamide). The other sequences degenerate to those described above which encode biologically active polypeptide of a receptor for modified low-density lipoprotein.

The sequence can be expressed in a recombinant transcription unit containing an inducible regulatory element derived from an operon of microorganism or virus. The present invention also provides expression vectors for producing useful quantities of a purified receptor for modified low-density lipoprotein. The vectors can comprise synthetic or cDNA derived DNA fragments encoding a mammalian receptor for modified low-density lipoprotein or bioequivalent homologues operably linked to regulatory elements derived from mammalian, bacterial, yeast, bacteriophage or viral genes. Useful regulatory elements are described in greater detail below. Following transformation, transfection or infection of appropriate cell lines, such vectors can be induced to express recombinant protein.

A mammalian receptor for modified low-density lipoprotein can be expressed in mammalian cells, yeast, bacteria, or other cells under the control of appropriate promoters. Cell-free translation systems could also be employed to produce the mammalian receptor for modified low-density lipoprotein using mRNAs derived from the DNA constructs of the present invention. Appropriate cloning and expression vectors for use with bacterial, fungal, yeast, and mammalian cellular hosts are described by Pouwel et al. (*Cloning Vectors: A Laboratory Manual*, Elsevier, New York, 1985), the relevant disclosure of which is hereby incorporated by reference.

Various mammalian cell culture systems can be employed to express recombinant protein. Examples of suitable mammalian host cell lines include the COS-7 lines of monkey kidney cells, described by Gluzman (*Cell* 23:175, 1981), and other cell lines capable of expressing an appropriate vector, for example, C127, 3T3, CHO, HeLa and BHK cell lines. Mammalian expression vectors may comprise nontranscribed elements such as an origin of replication, a suitable promoter and enhancer, and other 5' or 3' flanking nontranscribed sequences, and 5' or 3' nontranslated sequences, such as necessary ribosome binding sites, a polyadenylation site, splice donor and acceptor sites, and termination sequences. DNA sequences derived from the SV40 viral genome, for example, SV40 replication origin, early promoter, enhancer, splice, and polyadenylation sites, may be used to provide the other genetic elements required for expression of a heterologous DNA sequence. Exemplary vectors can be constructed as disclosed by Okayama and Berg (*Mol Cell Biol.* 3, 280, 1983).

A useful system for stable high level expression of mammalian receptor cDNAs in C127 rat mammary epithelial cells can be constructed essentially as described by Cosman et al. (*Molecular Immunol.* 23:935, 1986).

Yeast systems, preferably employing Saccharomyces species such as *S. cerevisiae*, can also be employed for expression of the recombinant proteins of the present invention. Yeast of other genera, for example, Pichia or Kluyveromyces, has also been employed as production strains for recombinant proteins.

Generally, useful yeast vectors will include origins of replication and selectable markers permitting transformation of both yeast and *E. coli*, e.g., the ampicillin resistance gene (Amp$^r$) of *E. coli* and *S. cerevisiae* TRP1 gene, and a promoter derived from a highly expressed yeast gene to induce transcription of a downstream structural gene. Such promoters can be derived from yeast transcriptional units encoding highly expressed genes such as 3-phosphoglycerate kinase (PGK), α-factor, acid phosphatase, or heat shock proteins, among others. The heterologous structural sequence is assembled in appropriate reading frame with translation initiation and termination sequences, and, preferably, a leader sequence capable of directing secretion of translated protein into the extracellular medium. Optionally, the heterologous sequences can encode a fusion protein including an N-terminal identification peptide or other sequence imparting desired characteristics, e.g., stabilization or simplified purification of expressed recombinant product.

Useful yeast vectors can be assembled using DNA sequences from pBR322 (Amp$^r$ gene and origin of replication) for selection and replication in *E. coli* and yeast DNA sequences including a glucose-repressible alcohol dehydrogenase 2 (ADH2) promoter. The ADH2 promoter has been described by Russell et al. (*J. Biol. Chem.* 258:2674, 1982) and Beier et al. (*Nature* 300:724, 1982). Such vectors may also include a yeast TRP1 gene as a selectable marker and the yeast 2μ origin of replication. A yeast leader sequence, for example, the α-factor leader which directs secretion of heterologous proteins from a yeast host, can be inserted between the promoter and the structural gene to be expressed (see U.S. Pat. No. 4,546,082; Kurjan et al., *Cell* 30:933, 1982); and Bittner et al., *Proc. Natl. Acad. Sci. USA* 81:983, 1984).

The leader sequence may be modified to contain, near its 3' end, one or more useful restriction sites to facilitate fusion of the leader sequence to foreign genes.

Suitable yeast transformation protocols are known to those skilled in the art; an exemplary technique is described by Hinnen et al. (*Proc. Nati. Acad. Sci. USA* 75:1929, 1978), selecting for Trp$^+$ transformants in a selective medium consisting of 0.67% yeast nitrogen source, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone and 1% glucose supplemented with 80 μg/ml adenine and 80 μg/ml uracil. Deregulation of the ADH2 promoter occurs upon exhaustion of medium glucose. Crude yeast supernatants are harvested by filtration and held at 4° C. prior to further purification.

Useful expression vectors for bacterial use are constructed by inserting a DNA sequence encoding a mammalian receptor for modified low-density lipoprotein together with suitable translation initiation and termination signals in operable reading frame with a functional promoter. The vector will comprise one or more phenotypic selectable markers and an origin of replication to ensure growth within the host. Suitable prokaryotic hosts for transformation include *E. coli*, *Bacillus subtilis*, *Salmonella typhimurium* and various species within the genera Pseudomonas, Streptomyces, and Staphylococcus, although others may also be employed as a matter of choice.

Expression vectors are conveniently constructed by cleavage of cDNA clones at sites close to the codon encoding the N-terminal residue of the mature protein. Synthetic oligonucleotides can then be used to "add back" any deleted sections of the coding region and to provide a linking sequence for ligation of the coding fragment in appropriate reading frame in the expression vector, and optionally a codon specifying an initiator methionine.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example pKK223-3p (Pharmacia Fine Chemicals, Uppsala, Sweden) and pGEM1 (Projema Biotec, Madison, Wis, USA). These pBR322 "main chain" sections are combined with an appropriate promoter and the structural sequence to be expressed.

A particularly useful bacterial expression system employs the phage λP$_L$ promoter and c1857 thermolabile repressor. Plasmid vectors available from the American Type Culture Collection which incorporate derivatives of the λP$_L$ promoter include plasmid pHUB2, resident in *E. coli* strain JMB9 (ATCC 37092) and pPLc28, resident in *E. coli* RR1 (ATCC 53082). Other useful promoters for expression in *E. coli* include the T7 RNA polymerase promoter described by Studier et al. (*J. Mol. Biol.* 189:113, 1986), the lacZ promoter described by Lauer (*J. Mol. Biol. Appl. Genet.* 1:139–147, 1981) which is available as ATCC 37121, and the tac promoter described by Maniatis (*Molecular Cloning: A Laboratory Manual*, Cold Spring Harbor Laboratory, 1982, p412), which is available as ATCC 37138.

Following transformation of a suitable host strain and growth of the host strain to an appropriate cell density, the selected promoter is derepressed by appropriate means (e.g., temperature shift or chemical induction) and cells cultured for an additional period. Cells are typically harvested by centrifugation, disrupted by physical or chemical means, and the resulting crude extract retained for further purification. Cells are grown, for example, in a 10 liter fermenter employing conditions of maximum aeration and vigorous agitation. An antifoaming agent (Antifoam A) is preferably employed. Cultures are grown at 30° C. in the superinduction medium disclosed by Mott et al. (*Proc. Natl. Acad. Sci. USA* 82:88, 1985), alternatively including antibiotics, derepressed at a cell density corresponding to $A_{600}$=0.4–0.5 by elevating the temperature to 42° C., and harvested for 2–20 hours, preferably 3–6 hours after the upward temperature shift. The cell mass is initially concentrated by filtration or other means, then centrifuged at 10,000×g (10,000 G) for 10 minutes at 4° C., followed by rapidly freezing the cell pellet.

Preferably, purified mammalian receptors for modified low-density lipoprotein or bioequivalent analogues are prepared by culturing suitable host/vector systems to express the recombinant translation products of the synthetic genes of the present invention, which are then purified from culture media.

An alternative process for producing a purified receptor for modified low-density lipoprotein involves purification from cell culture supernatants or extracts. In this approach, a cell line which elaborates useful quantities of the protein is employed. Supernatants from such cell lines can be optionally concentrated using a commercially available protein concentration filter, for example, an Amicon or Millipore Falcon ultrafiltration unit. Following the concentration step, the concentrate can be applied to a suitable purification matrix as previously described. For example, a suitable affinity matrix can comprise a receptor for modified low-density lipoprotein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups.

Finally, one or more reversed-phase high performance liquid chromatography (RP-HPLC) steps employing hydrophobic RP-HPLC media, e.g., silica gel having methyl or other aliphatic groups, can be employed to further purify a receptor composition for modified low-density lipoprotein. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or gel filtration chromatography steps. Finally, high performance liquid chromatography (HPLC) can be employed for final purification steps. Microbial cells employed in expression of recombinant mammalian receptor for modified low-density lipoprotein can be disrupted by any convenient method, including freeze-thaw cycling, sonication, mechanical disruption or use of cell lysing agents.

Fermentation of yeast which expresses a mammalian receptor for modified low-density lipoprotein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

In its various embodiments, the present invention provides essentially homogeneous polypeptides of a recombinant mammalian receptor for modified low-density lipoprotein free of contaminating endogenous material.

Recombinant proteins of a receptor for modified low-density lipoprotein according to the present invention also include suitable peptide or protein sequences employed as aids to expression in microorganisms or purification of microbially expressed proteins.

Bioequivalent analogues of the proteins of this invention include various analogs, for example, truncated versions of a receptor for modified low-density lipoprotein wherein terminal residues or sequences, which exist in internal cell and are not needed for biological activity, are deleted.

As used herein, "mutant amino acid sequence" refers to a polypeptide encoded by a nucleotide sequence intentionally made variant from a native sequence. "Mutant protein" or "analog" means a protein comprising a mutant amino acid sequence. "Native sequence" refers to an amino acid or nucleic acid sequence which is identical to a wild-type or native form of a gene or protein.

The protein of a receptor for modified low-density lipoprotein can be digested with a protease to obtain a soluble peptide fragment. The soluble peptide fragment can also be obtained by expressing a part of a receptor for the modified low-density lipoprotein in *E. coli* or mammals according to a recombinant DNA method. The obtained fragments are also included in the present invention so long as the fragments have the definition, namely an activity of binding a modified low-density lipoprotein.

Using the obtained soluble receptor, a modified low-density lipoprotein can be inactivated by binding the lipoprotein with the soluble peptide fragment. Accordingly, the peptide fragment can be used to cure a disease caused by a modified low-density lipoprotein.

Examples of the present invention are described below. In the following Examples, the amino acid sequence of the receptor for modified low-density lipoprotein and the DNA sequence encoding the receptor were elucidated from a bovine aortic endothelial cell. After the sequences set forth in the SEQ ID NOS: 1 and 3 were elucidated, the amino acid sequence of a human endothelial receptor for modified low-density lipoprotein and the DNA sequence encoding the receptor (SEQ ID NO: 5) were elucidated more easily. The amino acid sequence of the receptor for modified low-density lipoprotein and the DNA sequence encoding the receptor can easily be elucidated from another mammalian endothelial cell in a similar manner.

In more detail, a DNA sequence encoding another mammalian endothelial receptor for modified low-density lipoprotein can be selected from poly(A)$^+$ RNA, which was extracted from another mammalian endothelial cell or other organisms. The selection can be conducted by a hybridization with the DNA sequences set forth in the SEQ ID NOS: 1, 3 and 5. One skilled in the art can easily elucidate the sequence, as is mentioned above. The situation is now different from the Example 1 where there were no clues to the target sequence.

The obtained sequence can easily be analyzed by referring to the SEQ ID NOS 1, 3and 5. The analysis can be conducted much easier than the Example 1 (where there were no sequences to be referred).

In the following Examples, an assay was conducted with respect to an activity of binding an oxidized low-density protein. The same assay can also be conducted with respect to an activity of binding an acetylated low-density protein.

EXAMPLE 1

A cDNA library was constructed by a reverse transcription of mRNA including poly(A)$^+$ RNA according to a procedure similar to that of Chomczynski et al. (*Biotechniques* 15, 532, 1993). The poly(A)$^+$ RNA was isolated from total RNA extracted from cultured bovine aortic endothelial cell. In more detail, the cells were dissolved in a solution of acidic guanidinium isocyanate/phenol. Chloroform was added to the solution, and the solution was centrifuged to separate an aqueous phase and an organic phase. The aqueous phase was recovered, and purified with alcohol sedimentation. Poly(A$^+$)RNA was isolated by oligo dT cellulose chromatography and double-stranded cDNA was prepared by a method similar to that of Gubler and Hoffman (*Gene* 25, 263, 1983). Briefly, the RNA was copied into cDNA by reverse transcriptase using either oligo dT or random oligonucleotides as primer. The cDNA was made double-stranded by incubation with *E. coli* DNA polymerase I and RNase H, and the ends made flush by further incubation with T4 DNA polymerase. BstXI linker was added to the blunt-ended cDNA, and then short chains were removed by a gel filtration chromatography using Sephacryl S-500HR. The cDNA was subcloned into a high expression plasmid vector for mammalian cells (pME18S). A schematic illustration of pME18S is shown in FIG. 1 (obtained from Dr. Maruyama of Tokyo Medical and Dental University).

The pME18S vector is a plasmid vector of 3.4 kb which contains a replication initiating point of SV 40 and a type I promoter of SV40/human T lymphocyte leukemic virus.

The bovine aortic cDNA library on pME18S was used to transform *E. coli* (ElectroMax DH 10B) to provide about 7×10$^5$ colonies. These recombinants were cultured in 500 ml of 2xYT at 37° C. The plasmid DNA was prepared by a CsCl density-gradient centrifugation. The prepared DNA was transfected into a sub-confluent mono-layer of monkey COS-7 cells using Lipofectamine. The cells were then grown in culture for three days to permit transient expression of the inserted sequences. The cell monolayers in a plate were assayed for modified low-density lipoprotein uptake as follows.

To the plate was added 5 ml of DMEM medium with 10% fetal bovine serum (FBS) containing 15 µg of oxidized low-density lipoprotein labeled with DiI, and the plate was incubated for 12 hours at 37° C. at 5% $CO_2$. This medium was then discarded, and the plate was twice washed with PBS (pH 7.4). The cells were separated from the plate by tripsinization. The cells were applied to FACS to measure fluorescence of DiI and to recover the cells showing high fluorescent intensity. Plasmid was extracted from the recovered cells. The procedures were repeated four times. About 7×10$^5$ recombinants were screened from the library as is mentioned above. Thus COS-7 cells were transfected with a single clone pBLOX-1 which is capable of inducing expression of a receptor for oxidized low-density lipoprotein.

Figure 2:
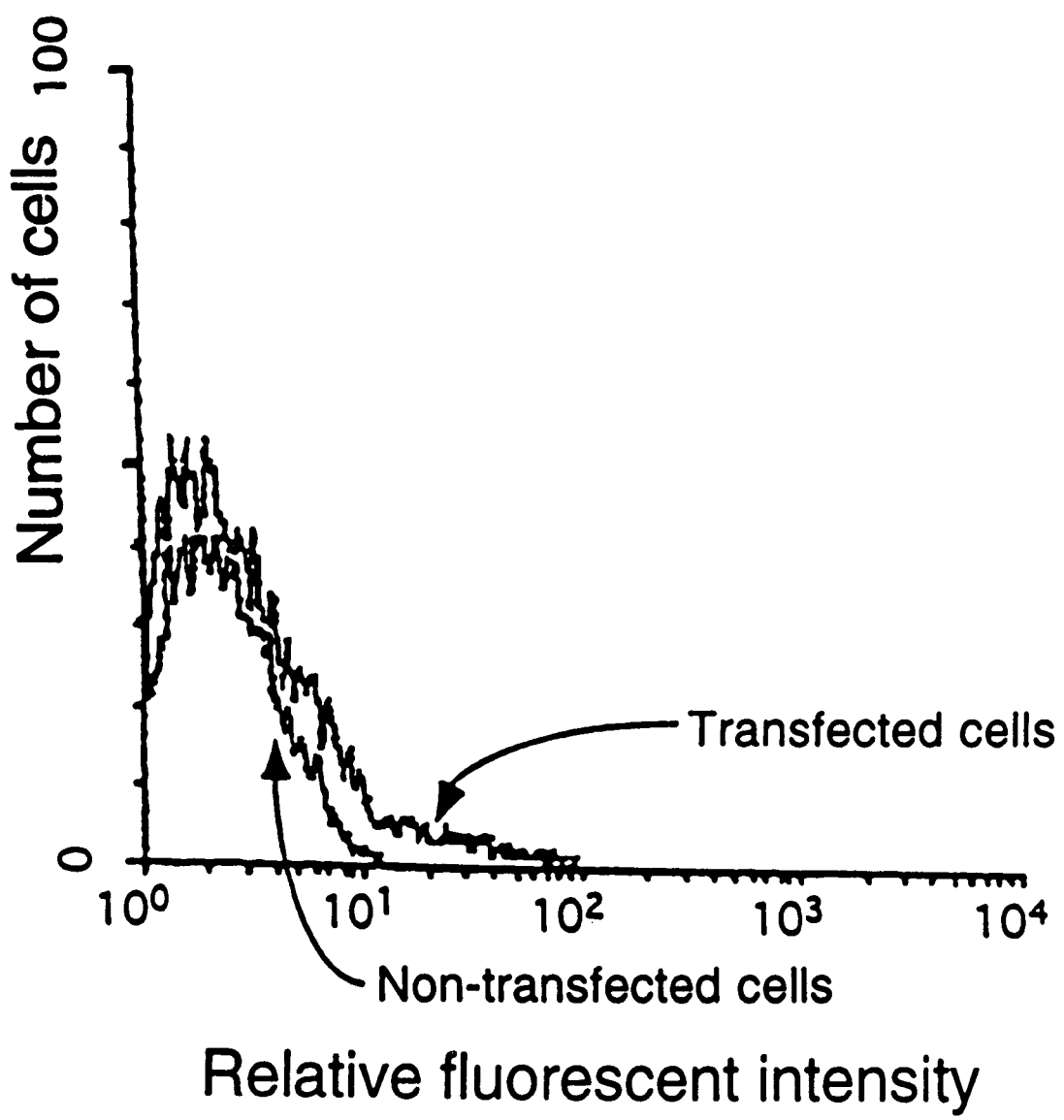
FIG. 2 is a graph showing the fluorescent intensity distribution of COS-7 cells which have been transfected with pBLOX-1 and a control COS-7 cell which has not been transfected. The intensity was measured by FACS.

FIG. 2 is a graph showing the fluorescent intensity distribution of COS-7 cells which have been transfected with pBLOX-1 and a control COS-7 cell which has not been transfected. The intensity was measured by FACS.

The inserted fragments of clone BLOX were subcloned to BluescriptII SK-plasmid, and its DNA sequence was determined according to the dideoxy method (see Sanger et al., *Proc. Natl. Acad. Sci. USA*, 74, 5463, 1977).

EXAMPLE 2

Expression in tissues by northern blots using receptor cDNA

Poly(A)$^+$ RNA was extracted from various bovine tissues in the same manner as is mentioned above. Each 5 µg of the RNAs was separated using formaldehyde/1.1% agarose gel electrophoresis, and transferred to gene screen plus membrane (NEN, DuPont). Then, 1.8 kb of cDNA fragments was labeled by α-$^{32}$P-dCTP according to a random priming method to 8×10$^8$ c.p.m./mg, and used as a probe. Hybridization was carried out at 60° C. in a solution of 1M sodium chloride, 1% SDS and 250 µg salmon sperm DNA. The membrane was washed with 2× SSC/1% SDS. Autoradiography was carried out for 8 hours.

Northern blots were carried out with respect to poly(A)$^+$ RNAs extracted from 11 bovine tissues. As the results, a large amount of modified low-density lipoprotein receptor mRNA was expressed in cultured endothelial cells and lung.

EXAMPLE 3

Expression of a receptor for modified low-density lipoprotein by CHO-K1 cell

The cells expressing a receptor for modified low-density lipoprotein were prepared using an expression vector pSV2bsr and the modified low-density lipoprotein receptor expression plasmid pBLOX-1. The pSV2bsr vector contains a bs$^r$ (blasticidin S-resistance) gene and a promoter derived from SV40 virus.

CHO (chinese hamster ovary) K1 cells were cultured as a subconfluent monolayer in a HamF12 medium containing 10% FBS.

The CHO-K1 cells were transfected with the modified low-density lipoprotein receptor expression plasmid pBLOX-1 and pSV2bsr using Lipofectamine. After 24 hours, the transfected cells were subcultured in an area about 10 times as large as the previous area. After 24 hours, the cells were well adhered, and the medium was replaced with a medium containing 5 µg of blasticidin S.

Thus only the cells transfected with bsr gene into genome grew, and their colony was formed.

The well grown colonies were detached using trypsin according to the penicillin cup method, and subcultured in 12 well plate using the same DMEM medium.

Figure 3:
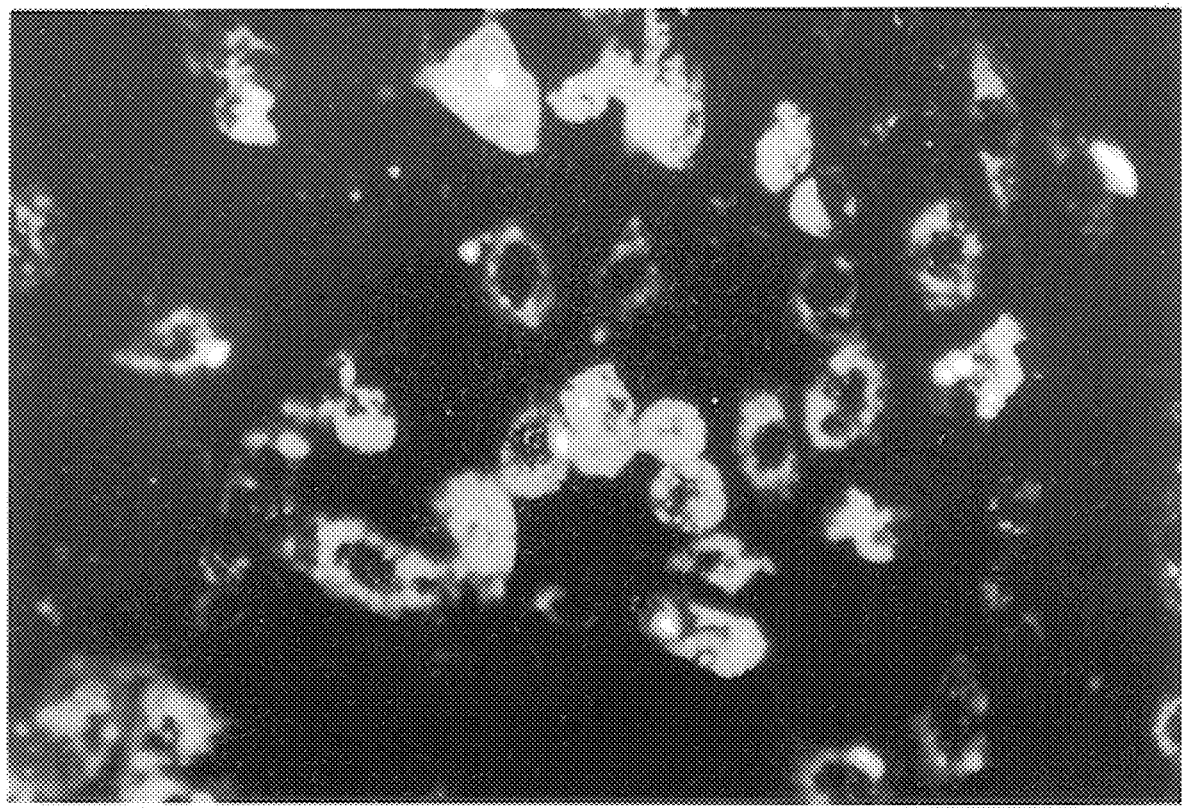
FIG. 3 is a fluorescent micrograph showing increase of fluorescent intensity in cytoplasm caused by incubation with DiI-labeled modified low-density lipoprotein.

Thus isolated clonal cells expressed a receptor for modified low-density lipoprotein, which was confirmed by a fluorescent microscope. The increase of fluorescent intensity was observed by the microscope. The increase was caused by incorporation of modified low-density lipoprotein labeled with DiI. FIG. 3 is the fluorescent micrograph.

EXAMPLE 4

Preparation of soluble modified low-density lipoprotein receptor

A cDNA fragment covering the extracellular domain of modified low-density lipoprotein (Base Nos. 160–813 in the SEQ ID NO: 1) was amplified by PCR with a pair of primers (5'-gcggatcctgtgctctcaatagattcgc-3' and 5'-ggggatcctgatctcataaagaaacag-3' SEQ ID NO: 7 and SEQ ID NO: 8, respectively) tagged with a BamHI restriction site. Amplified fragment was digested with BamHI and subcloned into the BamHI site of pQE10 (Qiagen), which expresses a protein tagged with six repeats of histidine in *E. coli*. The plasmid was transformed into an *E. coli* strain, XL-2Blue, and was cultured while shaking at 37° C. in 2xYT medium. When the absorbance at 600 nm was 0.6, 1 mM of IPTG (isopropylthio-β-D-galactoside) was added to the medium. The culture was further continued at 30° C. for 20 hours. E. coli was recovered by a centrifugation, was dissolved in 6M guanidine hydrochloride, 0.1M sodium dihydrogen phosphate and 0.01M Tris (pH 8.0). Insoluble materials were removed by a centrifugation, and soluble modified low-density lipoprotein receptor was adsorbed on Ni-NTA Agarose (Qiagen). Ni-NTA Agarose was washed with 8M urea, 0.1M sodium dihydrogen phosphate and 0.01M Tris (pH 8.0) and with 8M urea, 0.1M sodium dihydrogen phosphate and 0.01M Tris (pH 6.3). Soluble modified low-density lipoprotein receptor was eluted and purified with 8M urea, 0.1M sodium dihydrogen phosphate, 0.01M Tris and 0.1M EDTA (pH 6.3). The soluble modified low-density lipoprotein receptor was confirmed to be a homogeneous sample by using SDS-PAGE.

The other tags such as GST or c-myc can be used. The other purification methods such as a method using an antibody can also be used. Further, soluble modified low-density lipoprotein receptor can be prepared by recombinant DNA procedures using an appropriate mammalian expression vector.

EXAMPLE 5

Preparation of anti-LOX-1 antibody

The sequence encoding the extracellular domain (amino acids 61–270) of bovine LOX-1 cDNA was amplified by a polymerase chain reaction with a pair of primers (5'-ggggatcctgatctcataaagaaacag-3' and 5'-gcggatcctgtgctctcaatagattcgc-3'SEQ ID NO: 7 and SEQ ID NO: 8, respectively) tagged with a BamHI restriction site. The amplified cDNA fragment was digested with BamHI, and subcloned into BamHI sites of pQE10 vector (Qiagen). Protein synthesis and purification of the extracellular domain were conducted in QIA express system (Qiagen). In more detail, an E. coli strain, XL-2 blue (Stratagene) was transformed by the plasmid, and was cultured in 2xYT medium. The protein synthesis was induced with isopropylthio-β-D-galactoside. The cells were recovered by a centrifugation, and dissolved in 6M guanidine hydrochloride, 0.1M sodium phosphate and 0.01M Tris HCl (pH 8.0). A column chromatography was conducted with Ni-NTA resin column (Qiagen). The column was washed with 8M urea, 0.1M sodium phosphate and 0.01M Tris HCl (pH 6.3). Protein was eluted with 8M urea, 0.1M EDTA, 0.1M sodium phosphate and 0.01M Tris HCl (pH 6.3). The buffer was replaced with saline buffered with a phosphate salt by Centriprep 10 (Amicon). The protein was emulsified with the same volume of complete Freund's adjuvant. Rabbits were immunized by intracutaneous injection of the emulsion into the skin between blade bone and spine every two weeks.

Immunoblot

Cultured bovine aortic endothelial cells were directly solubilized in a sample buffer of SDS-PAGE. The extracts were separated by SDS-PAGE and blotted onto nylon membranes. After blocking with Block Ace (Snow Brand Milk Products Co., Ltd.), immunostaining of the membranes with an antibody, which was obtained from the above-mentioned rabbits, was performed using peroxidase-conjugated avidin-biotin complex and immunostain kit (Vector).

INDUSTRIAL APPLICABILITY

An object of the present invention is to elucidate the structure of a vascular endothelial receptor for modified low-density lipoprotein and to thereby provide a DNA sequence encoding the vascular endothelial receptor for modified low-density lipoprotein.

Another object of the invention is to provide a process for production of a vascular endothelial receptor for modified low-density lipoprotein or an analogue thereof.

A further object of the invention is to provide a protein composition containing vascular endothelial receptor for modified low-density lipoprotein or an analogue thereof.

---

We claim:

1. An isolated DNA sequence comprising a DNA sequence encoding a mammalian vascular endothelial receptor for modified low-density lipoprotein, said sequence being selected from the group consisting of SEQ ID NO: 1, SEQ ID NO: 3, SEQ ID NO: 5, a DNA sequence encoding SEQ ID NO: 2, a DNA sequence encoding SEQ ID NO: 4, and a DNA sequence encoding SEQ ID NO: 6.

2. An isolated DNA sequence encoding an amino acid sequence of amino acid Nos. 140 to 270 in SEQ ID NO: 2 SEQ ID NO: 4 or SEQ ID NO: 6.

3. An isolated DNA sequence encoding a mammalian vascular endothelial receptor for modified low-density lipoprotein, said sequence being set forth in SEQ ID NO: 1, SEQ ID NO: 3 or SEQ ID NO: 5.

4. An isolated DNA sequence comprising a recombinant transcriptional unit comprising inducible regulatory expression elements derived from a microbial or viral operon operably linked to a sequence selected from the group consisting of SEQ ID NO: 1, SEQ ID NO: 3, SEQ ID NO: 5, a DNA sequence encoding SEQ ID NO: 2, a DNA sequence encoding SEQ ID NO: 4, and a DNA sequence encoding SEQ ID NO: 6.

5. A process for production of a vascular endothelial receptor for modified low-density lipoprotein, which comprises transfecting the recombinant transcriptional unit of claim into a host cell and culturing the cell under conditions promoting expression.

6. A recombinant expression vector which contains a DNA sequence encoding a mammalian vascular endothelial receptor for modified low-density lipoprotein, said sequence being set forth in SEQ ID NO: 1, SEQ ID NO: 3 or SEQ ID NO: 5.

7. A purified protein composition containing a vascular endothelial receptor for modified low-density lipoprotein which is produced by a recombinant cell culture, said receptor having an amino acid sequence selected from the group consisting of SEQ ID NO: 2, SEQ ID NO: 4, and SEQ ID NO 6.

8. A purified peptide comprising an amino acid sequence of amino acid Nos. 140 to 270 in SEQ ID NO: 2, SEQ ID NO: 4 or SEQ ID NO: 6.

9. An isolated agent for detecting modified low-density lipoprotein, wherein the agent comprises a vascular endothelial receptor for modified low-density lipoprotein, said receptor having an amino acid sequence selected from the group consisting of SEQ ID NO: 2, SEQ ID NO: 4, and SEQ ID NO 6.

* * * * *